United States Patent
Kieturakis et al.

(10) Patent No.: US 10,779,806 B2
(45) Date of Patent: Sep. 22, 2020

(54) CABLE SHEATHS AND ASSEMBLIES FOR USE IN CURVED MEDICAL AND OTHER TOOLS

(71) Applicants: Maciej J. Kieturakis, Los Altos Hills, CA (US); Ronan L. Jenkinson, Walnut Creek, CA (US)

(72) Inventors: Maciej J. Kieturakis, Los Altos Hills, CA (US); Ronan L. Jenkinson, Walnut Creek, CA (US)

(*) Notice: Subject to any disclaimer, the term of this patent is extended or adjusted under 35 U.S.C. 154(b) by 0 days.

(21) Appl. No.: 15/730,081

(22) Filed: Oct. 11, 2017

(65) Prior Publication Data

US 2018/0280009 A1    Oct. 4, 2018

Related U.S. Application Data (60) Provisional application No. 62/407,394, filed on Oct. 12, 2016.

(51) Int. Cl.

| | |
|---|---|
| A61B 5/00 | (2006.01) |
| A61B 17/00 | (2006.01) |
| A61B 10/04 | (2006.01) |
| B25J 11/00 | (2006.01) |
| B23K 26/364 | (2014.01) |
| B23K 26/38 | (2014.01) |
| B23K 26/40 | (2014.01) |
| B23K 101/06 | (2006.01) |
| B23K 103/04 | (2006.01) |

(52) U.S. Cl.
CPC ........ *A61B 17/00234* (2013.01); *A61B 10/04* (2013.01); *B23K 26/364* (2015.10); *B23K 26/38* (2013.01); *B23K 26/40* (2013.01); *B25J 11/008* (2013.01); *A61B 2017/00314* (2013.01); *A61B 2017/00323* (2013.01); *A61B 2017/00526* (2013.01); *A61B 2017/00991* (2013.01); *B23K 2101/06* (2018.08); *B23K 2103/05* (2018.08)

(58) Field of Classification Search
CPC .............. A61B 17/00234; A61B 10/04; A61B 2017/00323; A61B 2017/00526; A61B 17/00991; A61B 2017/00314; B25J 11/008; B23K 26/364; B23K 2101/06; B23K 2103/05; B23K 26/38; B23K 26/40
See application file for complete search history.

(56) References Cited

U.S. PATENT DOCUMENTS

| | | | |
|---|---|---|---|
| 338,310 A | 3/1886 | Smith | |
| 1,276,117 A | 8/1918 | Theodore | |
| 1,911,470 A | 5/1933 | Rosner | |
| 3,546,961 A * | 12/1970 | Marton | ................... B63C 11/26 74/502.5 |
| 4,328,839 A * | 5/1982 | Lyons | ..................... E21B 17/20 138/120 |
| 7,784,376 B2 | 8/2010 | Wen | |
| 8,497,427 B2 | 7/2013 | Wen | |

(Continued)

*Primary Examiner* — Scott M. Getzow
(74) *Attorney, Agent, or Firm* — Wilson Sonsini Goodrich & Rosati (57) ABSTRACT

A flexible cable sheath includes an outer sleeve, an inner sleeve, and a flexible cable passing through the inner sleeve. The outer sleeve has a plurality of individual segments which are coupled to bend and have limited axial separation. By tensioning the inner sleeve relative to the outer sleeve, the resulting assembly has improved dimensional stability and torsional rigidity.

18 Claims, 11 Drawing Sheets

(56) References Cited

U.S. PATENT DOCUMENTS

| | | |
|---|---|---|
| 8,607,541 B1 | 12/2013 | Cavuoti |
| 9,144,370 B2 | 9/2015 | Kato et al. |
| 2012/0116362 A1 | 5/2012 | Kieturakis |
| 2016/0081752 A1 | 3/2016 | Kieturakis |
| 2016/0324412 A1* | 11/2016 | Hassidov ........... A61B 1/00089 |

* cited by examiner

CABLE SHEATHS AND ASSEMBLIES FOR USE IN CURVED MEDICAL AND OTHER TOOLS

CROSS-REFERENCE TO RELATED APPLICATIONS

This application claims the benefit of priority to provisional No. 62/407,394, filed Oct. 12, 2016, the entire content of which is incorporated herein by reference.

BACKGROUND OF THE INVENTION

1. Field of the Invention

The present invention relates generally to medical systems, tools, and methods. More particularly, the present invention relates to an improved cable assembly for use in systems and tools for single port laparoscopic access and other purposes.

In recent years, many open surgical procedures performed in the abdominal cavity have been replaced by minimally invasive procedures performed through several very small incisions using an endoscope, referred to as a laparoscope, inserted through one of the incisions. The other incisions are used for introducing surgical tools, and the abdominal cavity is inflated to create a space for performing the surgery. Such procedures are commonly called "laparoscopic", and can be used for gallbladder removal, hernia repair, hysterectomy, appendectomy, gastric fundoplication, and other procedures. Similar endoscopic, thoracoscopic and other procedures are performed in other body cavities without inflation.

A particular advance in such laparoscopic surgical procedures has been "single port" laparoscopy where a single access port is inserted, typically through the patient's umbilicus (navel). Access solely through the umbilicus is advantageous since it provides a superior cosmetic result. Introducing the laparoscope and all other tools necessary for the surgery through a single port, however, makes performance of the procedures more difficult. In particular, the use of conventional laparoscopic tools, which are typically straight, makes it difficult to approach a single target area in the treated tissue with two or more tools at the same time.

As an improvement over the use of straight laparoscopic tools in single port laparoscopic surgery, the construction and use of curved tools which define spaced-apart virtual insertion point while still passing through the single port are described in U.S. Patent Publications 2012/0116362 and 2016/0081752, commonly assigned with the present application and incorporated herein by reference.

Figure 1:
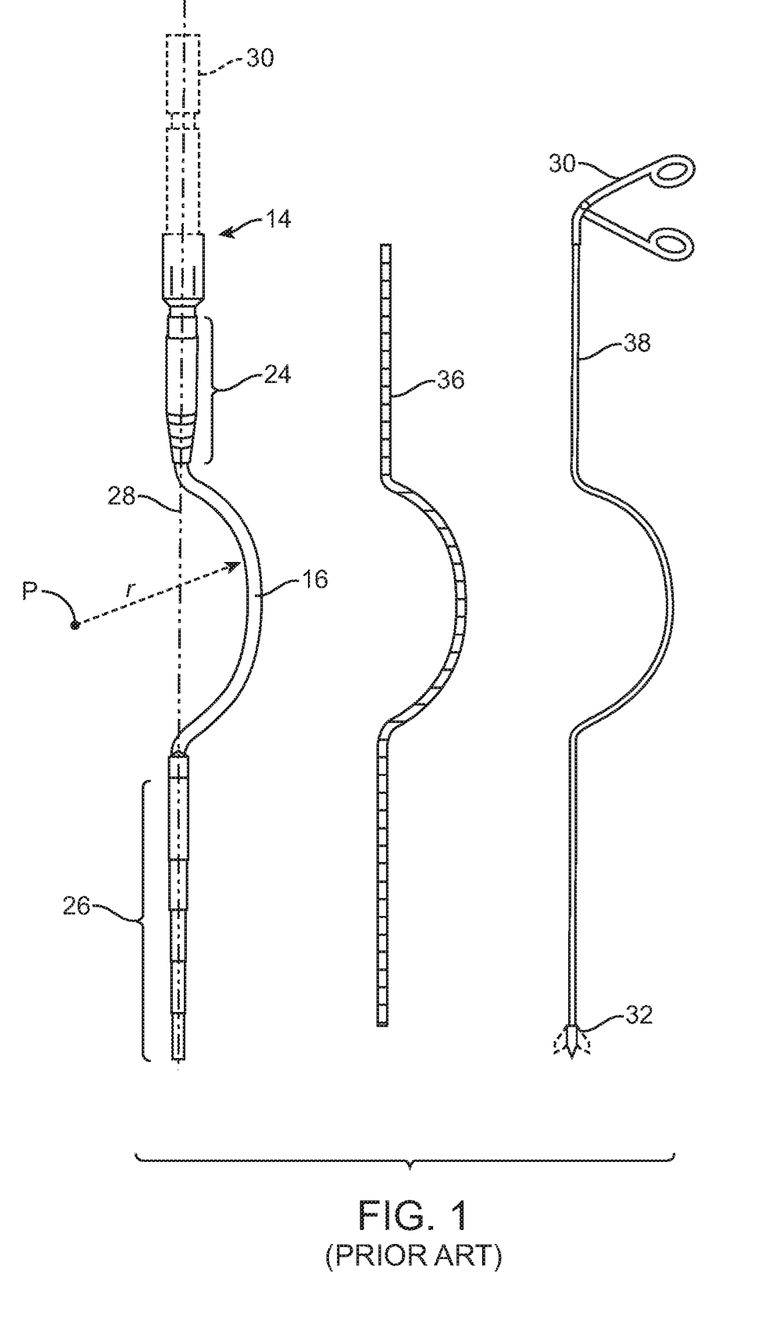
FIG. 1 illustrates a type of laparoscopic tool having a curved central region or segment which is particularly suited for use with the flexible cable sheaths and cable assemblies of the present invention.

As shown in FIG. 1 (FIG. 7 from US 2016/0081752), a tool 14 has forceps or another scissors-like end effector 32 which is actuated by a pivoting handle 30. The handle 30 will operate by pulling pull wire 38 which passes through a central lumen of a flexible cable 36. The assembly of the flexible cable 36 and pull wire 38 (often referred to as a "Bowden cable"), in turn, is located within a curved central segment 16 of the tool 14. The length of the cable 36 is intended be fixed and equal the length of the tool 14 with one of a pair of telescoping ends 24 and 26 fully extended (26 as illustrated) and the other fully contracted (24 as illustrated). In this way, pushing and pulling on the actuator 30 relative to the mid-portion 16/22 of the tool will cause one of the telescoping sections to elongate while the other foreshortens. Each telescoping section, however, will be able to cover and maintain axial rigidity of the cable 36 and wire 38 so that the tool maintains alignment along the axis 28 (with the exception of the curved central segment 16 of the tool). The curved central segment 16 passes through the single port, while the axis 28 passes through a virtual insertion point in the patient's abdominal wall, as described in both US 2012/0116362 and US 2016/0081752.

While use of the curved laparoscopic tools of US 2012/0116362 and US 2016/0081752 has significant advantages over the use of straight tools in single port laparoscopy, the need to pass through the curved central segment 16 of the tool requires a highly flexible cable, and such flexible cables can often lack dimensional stability, e.g. be axially stretchable or compressible, and lack torsional stiffness. Dimensional stability and torsion stillness are both desirable in the tools of US 2012/0116362 and US 2016/0081752.

For these reasons, it would be desirable to provide improved Bowden cables and other pull—push cable assemblies having both dimensional stability and torsional rigidity for use in laparoscopic tools and for other purposes.

Figure 2:
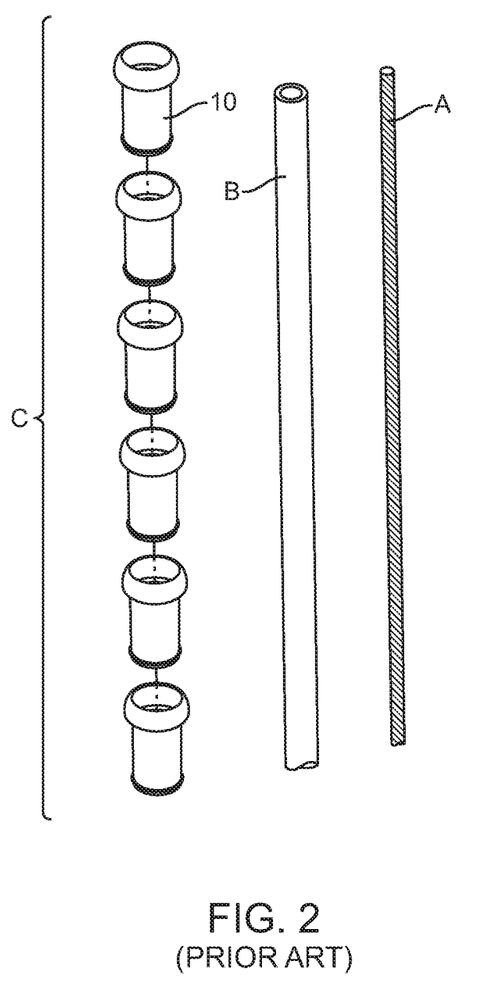
FIG. 2 illustrates a prior art flexible cable assembly.

One example of an improved Bowden cable is shown in FIG. 2, which is taken from FIG. 1 of U.S. Pat. No. 7,784,376. A cable assembly, which is intended for use in bicycles for brakes or gear shifters, includes a cable A, an inner protection tube B, and an external protection tube C. The external protection tube C comprises a plurality of individual sleeves 10. The sleeves are joined by rings and flanges which resist compression when the tube is straight but which do not hold the tube together in tension or bending, as can be seen in FIG. 6 of U.S. Pat. No. 7,784,376, which is not reproduced herein. While an improvement for bike cables, the cable design of U.S. Pat. No. 7,784,376 would not provide the dimensional stability and torsion stillness which are desirable in the tools of US 2012/0116362 and US 2016/0081752.

2. Description of the Background Art

US 2012/0116362, US 2016/0081752, and U.S. Pat. No. 7,784,376, have been described above. Other patents of interest include U.S. Pat. Nos. 9,144,370; 8,607,541; 8,497,427; 4,328,839; 3,546,961; 1,911,470; 1,276,117; and U.S. Pat. No. 338,310.

SUMMARY OF THE INVENTION

The present invention provides flexible cable sheaths or housings suitable for use in various push-pull cable assemblies, for example assemblies of the type commonly referred to as "Bowden cables." While the flexible cable sheaths of the present invention will be particularly useful for incorporation into surgical and other medical tools, such as laparoscopic tools, the flexible cable sheaths could also find use in a wide variety of other medical and non-medical applications, such as biopsy tools, bicycle cables, robotic control cables, and the like. The flexible cable sheaths of the present invention have structures which provide for flexibility and bendability while maintaining both dimensional stability and torsional rigidity. These flexible cable sheaths are particularly advantageous when used in tools having a curved shaft or other component through which the cable sheath must pass. Tension of the flexible cable sheaths of the present invention can be adjusted at the time of fabrication to accommodate any smooth, predefined curve present in such tools without significant loss of stability or torsional rigidity.

In a first aspect, the present invention provides a flexible cable sheath comprising an outer sleeve having a proximal end, a distal end, and a central lumen extending between said ends. The outer sleeve includes a plurality of individual segments, and axially adjacent individual segments are coupled in a manner which limits axial separation while allowing bending. An inner sleeve is disposed within the central lumen of the outer sleeve and has a proximal end, a distal end, and an inner lumen extending between said ends. The outer and inner sleeves are fixed to each other at their respective proximal and distal ends, and the outer sleeve is axially tensioned over the inner sleeve. In particular, the axial tensioning helps maintain the dimensional stability of the flexible cable sheath as the sheath may be advanced and retracted within a laparoscopic or other tool. The inner lumen of the inner sleeve is configured to slidably receive a push-pull cable, and the resulting flexible cable sheath and push-pull cable assembly can be used in a wide variety of laparoscopic and other medical tools which heretofore have employed more conventional push-pull cables, such as Bowden cable.

In a specific embodiment of the flexible cable sheaths of the present invention, the axially adjacent individual segments will be coupled in a manner which limits relative rotational movement in addition to relative axial motion. For example, the axially adjacent individual segments may be joined by tabs and slots where a tab on one individual segment is received in a slot on an adjacent individual segment. The tabs and slots are preferably configured to allow a limited relative axial movement between the adjacent segments while substantially inhibiting torsional movement. Usually, at least two, and more commonly three, such tab and slot assemblies will be provided between each adjacent pair of independent segments, and the resulting arrangement will allow bendability in all directions (much like a universal joint) while still substantially inhibiting relative rotation between the adjacent segments. The tabs and slots may take any conventional form, such as T-tabs and T-slots, disc-like tabs and circular slots, and the like. Usually the tab and slot will be laser cut into a thin-wall metal or other tubular structure and will have sufficient axial clearance between axially abutting surfaces to permit the desired axial movement between adjacent axial segments to allow bending. The tube may have a wall thickness in the range from 0.5 mm to 2 mm for laparoscopic and other medical applications but can vary widely to non-medical uses. The tabs and slots will, however, have minimal lateral clearance in order to limit relative rotation of the adjacent axial segments. By forming the outer sleeve from a tube having a very thin wall, the outer sleeve will have a very thin cylindrical envelope which reduces the overall diameter of the flexible cable sheath. This is particularly important in laparoscopic tools where the use of very narrow profile tools is becoming widespread.

In other specific embodiments, the inner sleeve will comprise a helical coil having a very high axial compression load or column strength. The helical coil may comprise round wire, flat ribbon, or have any other conventional coil structure. Optionally, the inner sleeve could comprise counter-wound helical coils, but that would increase the diameter of the resulting cable sheath. While helical coils are subject to elongation, in the cable sheath constructions of the present invention, the outer sleeve will axially compress the inner coil sleeve in order to enhance the dimensional stability of the cable sheath assembly, in particular by minimizing any axial elongation or shortening of the cable sheath. In such assemblies, the tension load on the cable sheath will be borne by the outer sleeve (for push applications) which is under axial extension after fabrication. The compression load will be carried by the inner sleeve (for pull applications).

The flexible cable sheaths of the present invention will usually be used in combination with a push-pull cable which is slidably received within the inner lumen of the inner sleeve to form a push-pull cable assembly. Such push-pull cable assemblies can serve as the functional equivalent of a Bowden cable while having the advantages of dimensional stability and the controlled bendability as described elsewhere herein.

The push-pull cable assemblies of the present invention will find particular use in laparoscopic tools comprising a shaft having a distal end, a proximal end, and a central passage therethrough. The flexible push-pull cable sheaths, as described, pass through the central passage within the laparoscopic tool shaft with a distal end of the push-pull cable sheath extending beyond the distal end of the shaft and a proximal end of the push-pull cable sheath extending beyond the proximal end of the shaft. The push-pull cable is slidably received within the inner lumen of the inner sleeve, and a handle secured to the proximal end of the push-pull cable sheath is operatively coupled to a proximal end of the push-pull cable. A tool is secured to the distal end of the push-pull cable sheath, and is operatively coupled to a distal end of the push-pull cable so that tension applied to the push-pull cable actuates the tool.

In preferred examples, the shaft of the laparoscopic tool has a curved or arcuate section, e.g. a C-section as illustrated herein after. Tension on the outer sleeve of the push-pull cable sheath can be adjusted so that the axial segments of the flexible cable sheath are allowed to bend relative to each other while being advanced or retracted through the arcuate section while the entire length of the flexible push-pull cable sheath remains under tension and resists both stretching and axial compression.

In other aspects of the present invention, a lever on the handle of the laparoscopic tool is attached to the proximal end of the push-pull cable, and the lever is configured to selectively apply tension to the push-pull cable to actuate the tool.

In still further aspects of the present invention, a flexible push-pull cable sheath may be fabricated by patterning an outer sleeve to a plurality of axially adjacent segments. The axially adjacent segments are interlinked in a manner which allows limited axial separation and bending therebetween. An inner sleeve is secured within a lumen of the patterned outer sleeve, and the inner sleeve has a lumen configured to slidably receive a push-pull cable.

In such fabrication methods, the individual segments are often interlinked to limit relative rotational movement in addition to providing for controlled axial movement. In still further specific aspects of the fabrication methods, securing the inner sleeve within the lumen of the outer sleeve comprises axially tensioning the outer sleeve over the inner sleeve and thereafter fixing the outer and inner sleeves to each other at their respective proximal and distal ends to maintain said tensioning. While the outer and inner sleeves may be tensioned while both are in a linear configuration, the tensioning will usually occur while the inner sleeves and outer sleeve are held in a curved configuration, such as being held in a curved mandrel or other forming tool or jig. By tensioning when the axially adjacent individual segments of the outer sleeve are a curved configuration, the ability of the segments to form such a curve and use is maintained. In particular, if a given number of the axially adjacent segments are formed into a curve having a particular geometry, such as defined by the forming mandrel, then the resulting flexible cable sheath may be axially retracted and advanced within a tool having an identical curved region with different runs of the axially adjacent segments adapting to the curve as the sheath is moved.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 3:
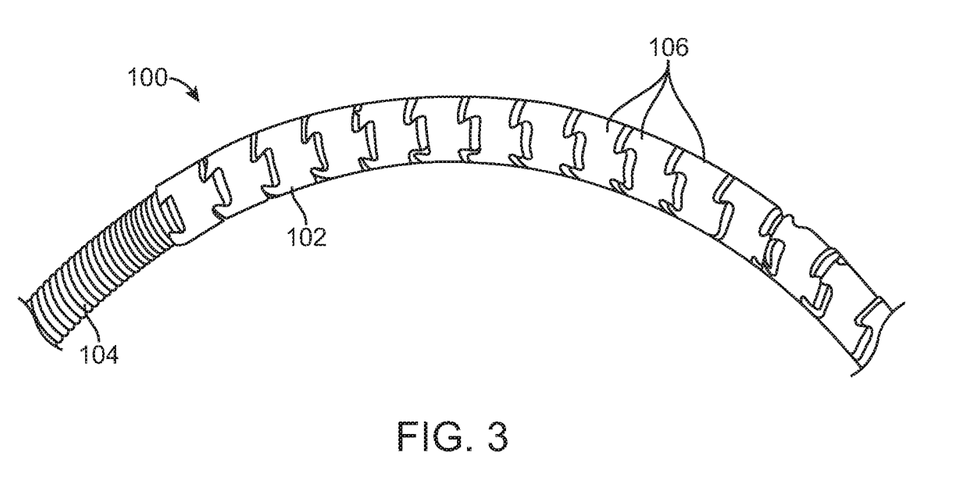
FIG. 3 illustrates a portion of an outer sleeve and a portion of an inner sleeve constructed in accordance with the principles of the present invention.
Figure 4:
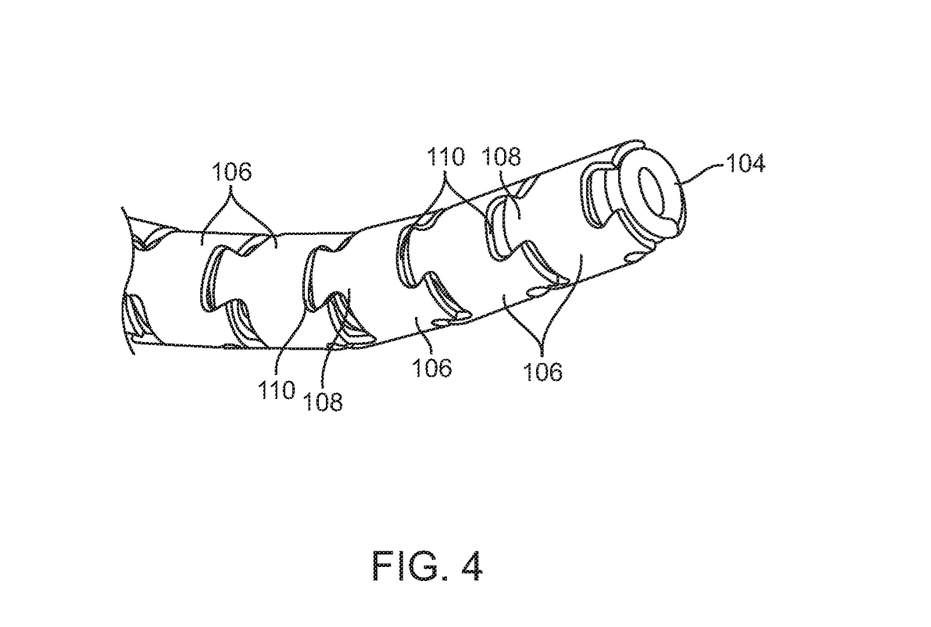
FIG. 4 is a detail of the sheath of FIG. 3 showing how a coil inner sleeve is disposed within a segmented outer sleeve.

As shown in FIGS. 3 and 4, a flexible cable sheath 100 constructed in accordance with the principles of the present invention comprises an outer sleeve 102 and an inner sleeve 104. The outer sleeve 102 includes a plurality of individual axially adjacent segments 106 which are joined together by tabs 108 and slots 110. As described in more detail below in connection with FIGS. 5-7D, the tabs and slots are formed to have an interference fit which permits a limited degree of axial motion and bending while preventing axial separation and limiting relative rotation.

Figure 5:
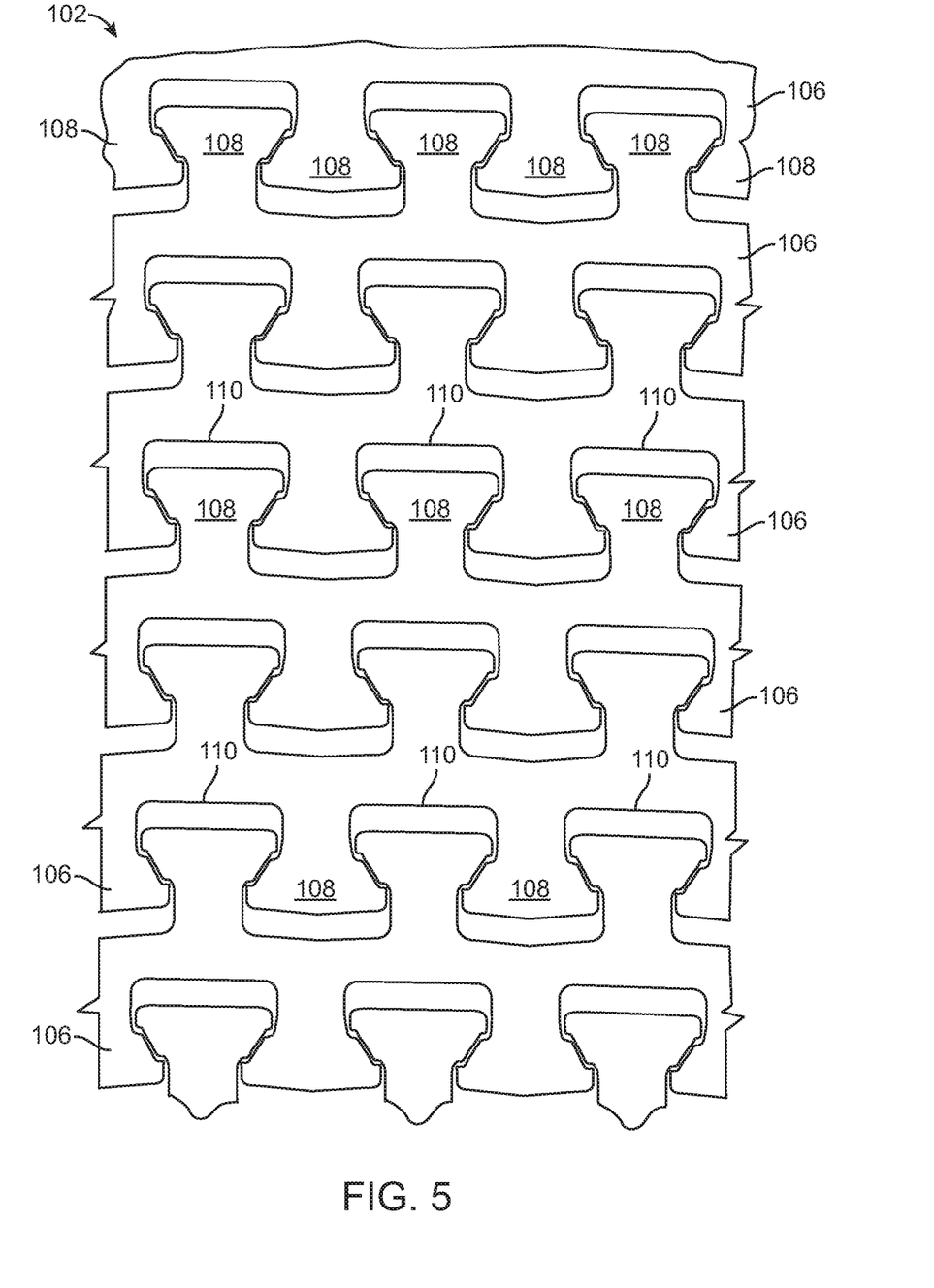
FIG. 5 is a "rolled-out" version of a portion of the outer sleeve of the flexible cable sheath of FIGS. 3 and 4.

Each pair of adjacent axial segments 106 in the outer sleeve 102 will have three pairs of tabs and slots connecting them, as best seen in FIG. 5. FIG. 5 is a "rolled out" representation of the outer sleeve 102 in the tubular form of the outer sleeve, each of the tabs 108 and slots 110 will be separated by 120° which has been found to allow a suitable degree of controlled bendability between the adjacent segments.

Figure 6:
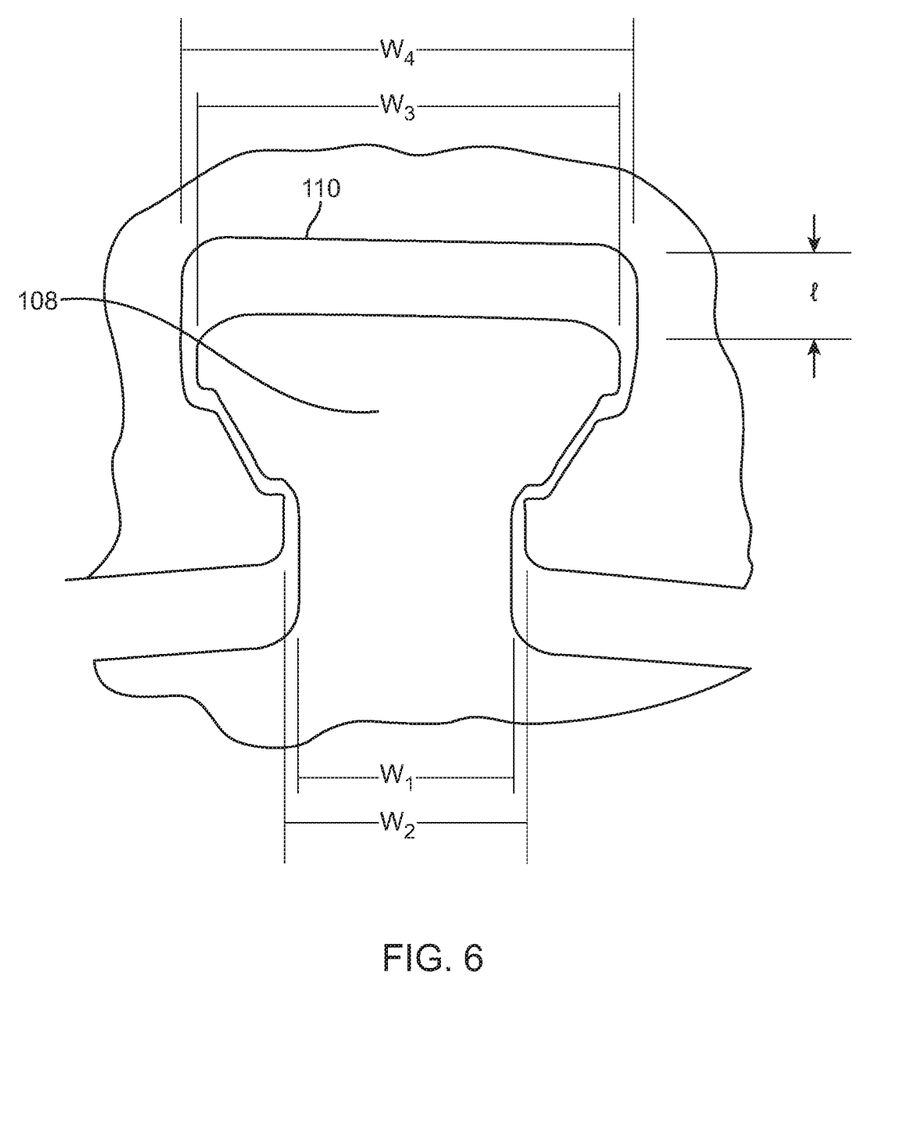
FIG. 6 is a detailed view of a single tab and slot of the outer sleeve of the flexible cable sheath of FIGS. 3-5.

Referring now to FIG. 6, the outer sleeve 102 is preferably formed by laser cutting or otherwise patterning a thin wall tube, typically a stainless steel tube having an outer diameter in the range from 2 mm (millimeters) to 10 mm, usually from 3 mm to 5 mm, and a length in the range from 10 centimeters (cm) to 45 cm, usually in the range from 15 cm to 25 cm. The individual tabs 108 and slots 110 will be cut to have a clearance so that each tab may move within the boundary or periphery created by the slot 110. Exemplary dimensions for the tabs and slots with the desired clearances for small diameter devices of the type used in laparoscopic and other surgical procedures are shown in Table 1 below. These dimensions may be much larger for larger devices and systems.

TABLE 1

EXEMPLARY DIMENSIONS (FIG. 6)

|  | Broad Range | Specific Range |
| --- | --- | --- |
| $W_1$ | 0.75 mm to 2 mm | 1 mm to 1.5 mm |
| $W_2$ | 1 mm to 2 mm | 1.25 mm to 1.75 mm |
| $W_3$ | 2 mm to 3 mm | 2.25 mm to 2.75 mm |
| $W_4$ | 2 mm to 3.5 mm | 2.5 mm to 3 mm |
| 1 | 0.25 mm to 1 mm | 0.25 mm to 0.75 mm |

Figure 7A:
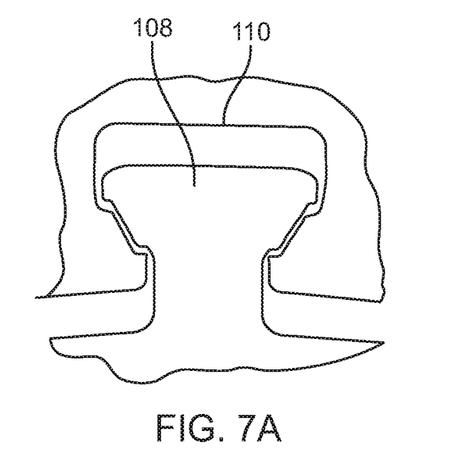
FIG. 7A through 7D illustrate the tab and slot of FIG. 6 shown in various bending and axially extended configurations.
Figure 7B:
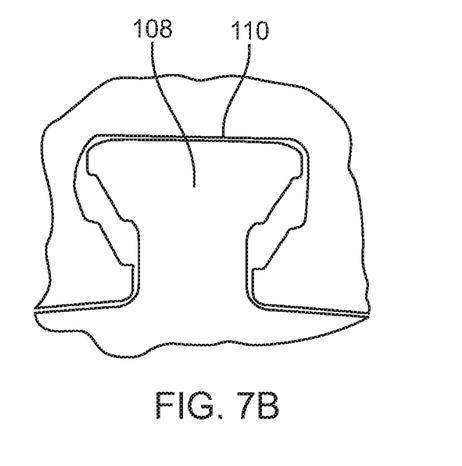
Figure 7C:
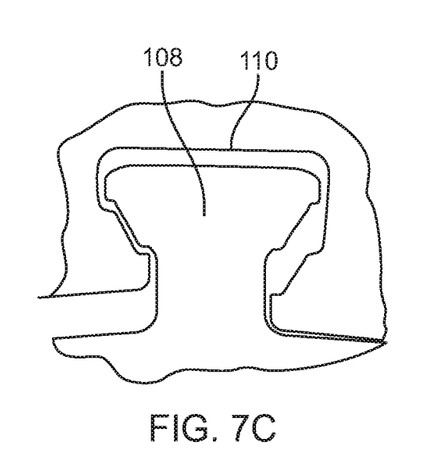
Figure 7D:
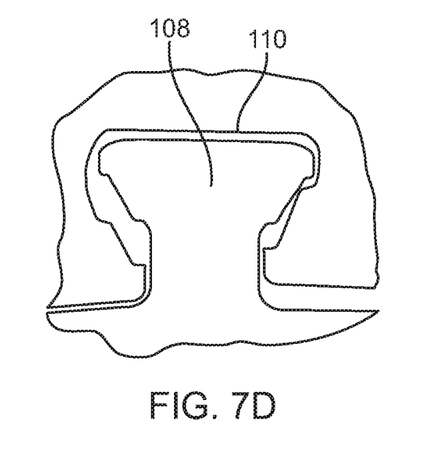

As illustrated in FIGS. 7A-7D, the clearance between the tab 108 and slot 110 allows significant relative movement between the portions of the adjacent segments 106 joined by these slots. For example, as shown in FIG. 7A, the slots may be axially separated until the lower region of the tab 108 nests and the corresponding surfaces of the slot 110. Conversely, when placed under compression, the upper surface of the tab 108 may engage a lower surface of the top of the slot 110, as shown in FIG. 7B. In addition to axial motion, the geometries of the tab 108 and slot 110 allow bending or pivoting between the adjacent segments 106 in either direction, as shown in FIGS. 7C and 7D, respectively. As each adjacent segment 106 is joined by three tab/slot assemblies, of course, each of the three tabs and slots adjoining the adjacent segments will be in a different configuration when the segments are being bent relative to each other. With the illustrated geometries, the tab 108 and slots 110 will allow the adjacent segments 106 to bend in any direction without significant constraint. Also, the tabs and slots will allow the adjacent segments 106 to move axially apart by the full clearance between them as shown in FIG. 7A when the inner sleeve applies tension to the outer sleeve, as will be described in detail below with respect to fabrication of the flexible cable sheaths of the present invention.

Figure 8:
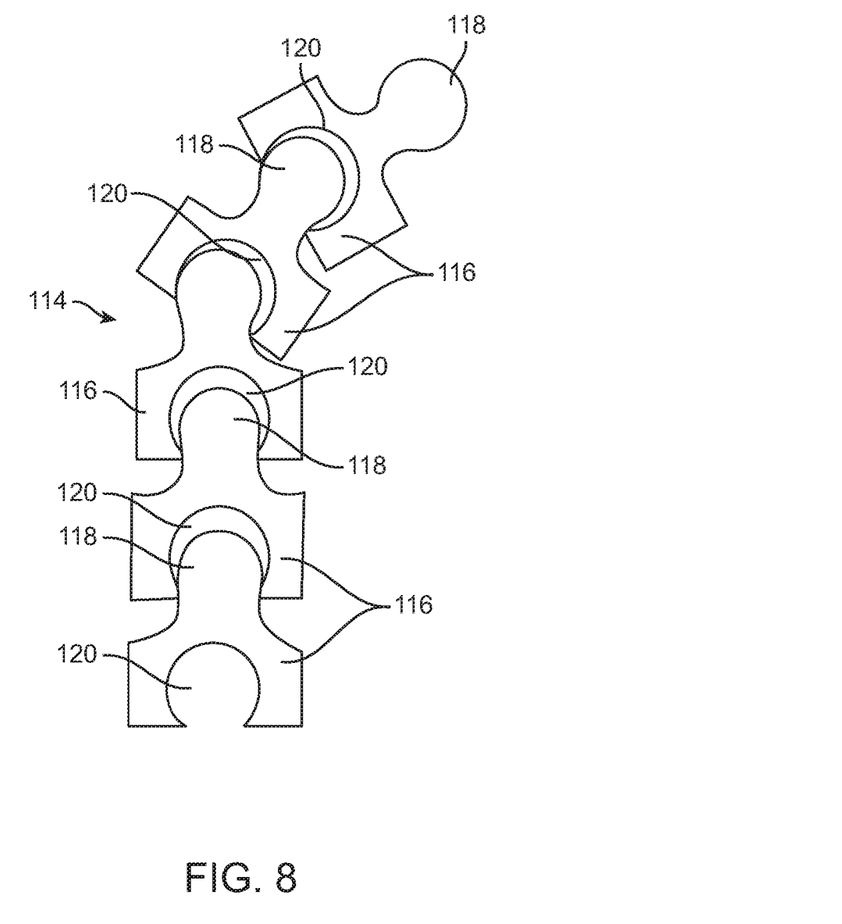
FIG. 8 illustrates an alternative tab and slot configuration for an outer sleeve according to the present invention.
Figure 9:
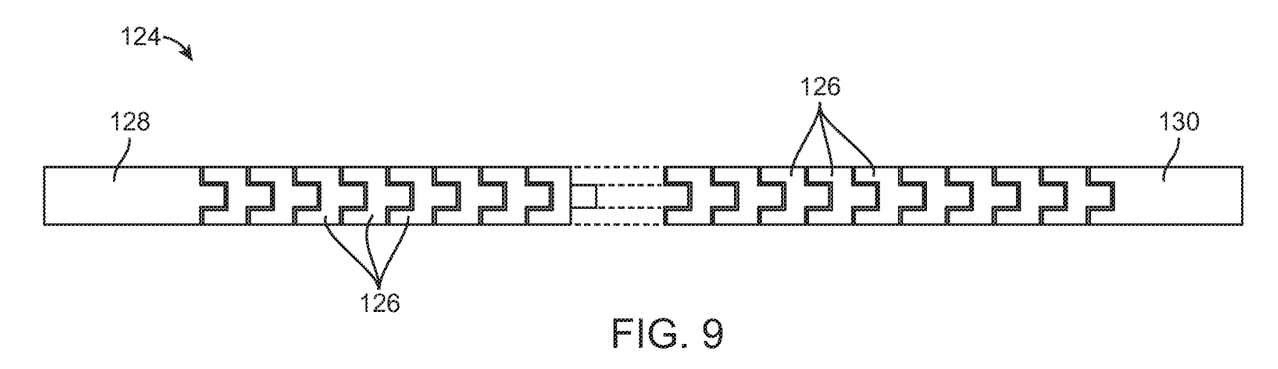
FIGS. 9-13 illustrate a method for fabricating a flexible cable sheath in accordance with the principles of the present invention.
Figure 10:
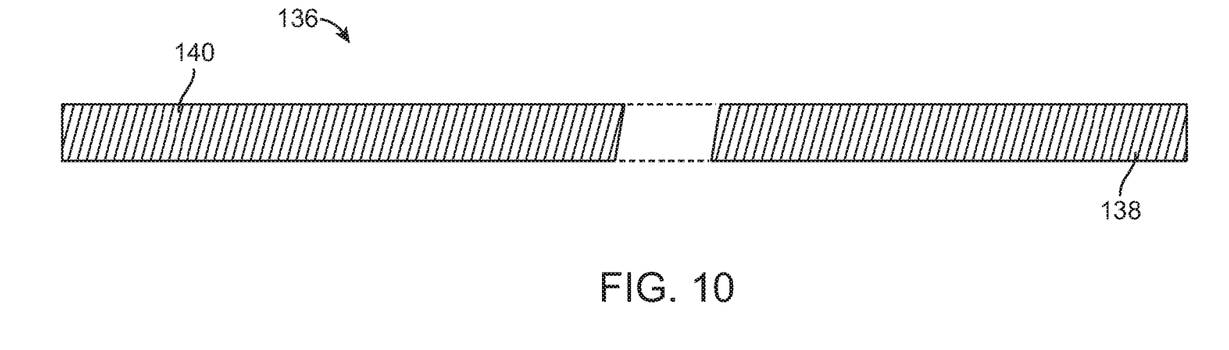

While a preferred tab 108 and slot 110 configuration is shown in the figures described above, tabs and slots can take a variety of different configurations, as shown for example in FIG. 8 where tabs 118 have generally circular peripheries and slots 120 have generally circular but larger peripheries. Such an alternative sleeve 114 comprises a plurality of adjacent segments 116.

Figures 11, 12:
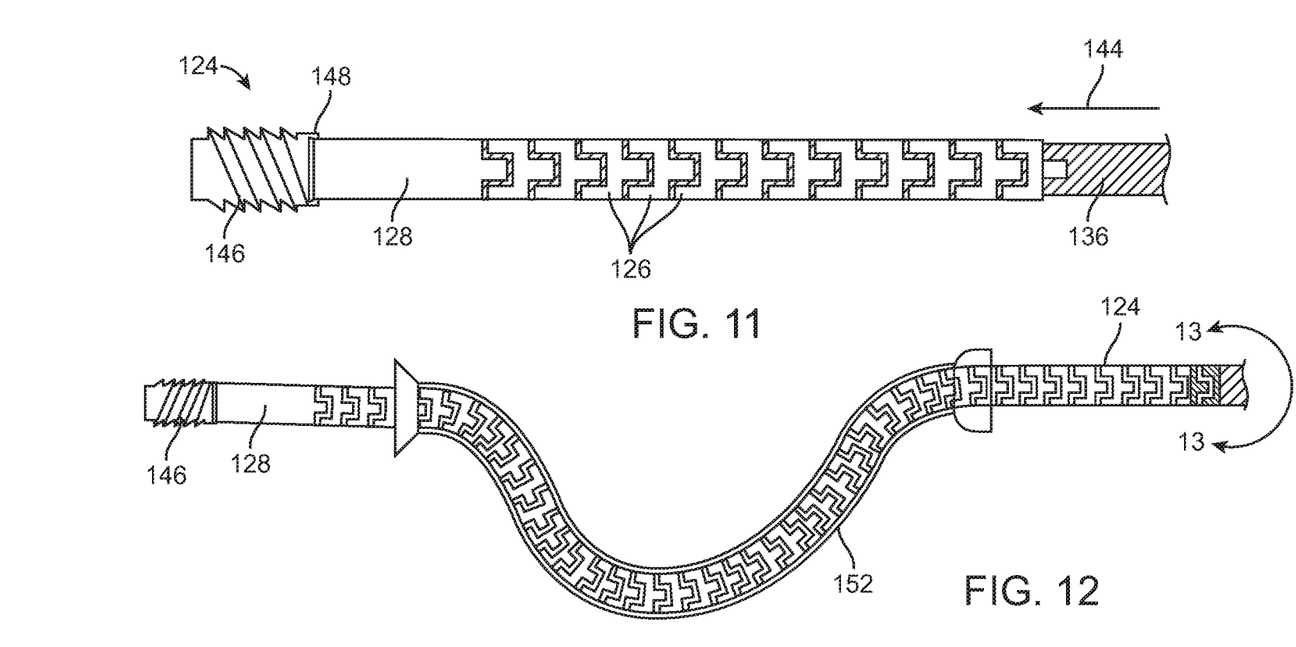

Referring now to FIGS. 9 through 13, a method for fabricating a flexible cable sheath in accordance with the principles of the present invention will be described. An outer sleeve 124 having a plurality of segments 126, a proximal rigid end segment 128 and a distal rigid end segment 130 is provided. The outer sleeve 124 may have any of the configurations described previously or may have another configuration. An inner sleeve 136 having a proximal end 138 and distal end 140 is also provided. The inner sleeve will typically be a helical coil with closely wound turns so that it will resist axial compression. Optionally, the inner sleeve 136 will be coated or encapsulated in a polymer to enhance stability and facilitate movement within the lumen of the outer sleeve 124. As shown in FIG. 11, assembly of the flexible cable sheath begins by inserting the distal end 140 of the inner sleeve 136 into the inner lumen of the outer sleeve 124. The distal end of the inner sleeve 136 is then secured to the distal end of the outer sleeve 124, typically by soldering 148, and optionally a threaded ring 146 or other tool connector element can be attached at this point in the fabrication process.

The assembly of the outer sleeve 124 and the inner sleeve 136 having only their distal ends connected is then introduced into a curved forming mandrel 152, as shown in FIG. 12. The dimensions of the curved region of the mandrel 152 will be similar and preferably identical to those of a tool in which the flexible cable sheath is to be used, such as the laparoscopic tool 14 shown in FIG. 1 where the curve 152 will be identical to the curved section 16 of that laparoscopic tool.

Figure 13:
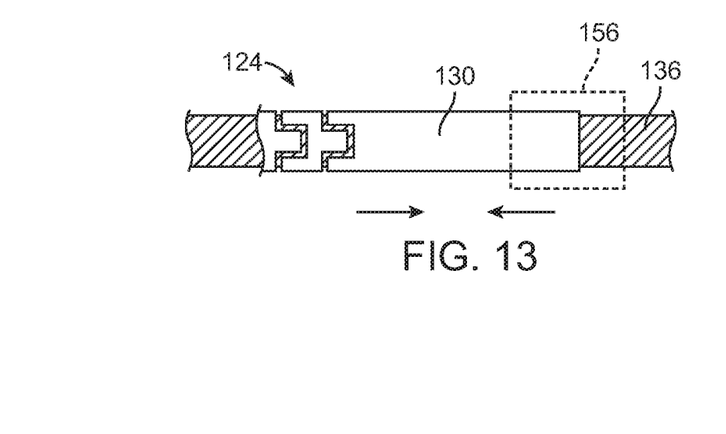
Figure 14A:
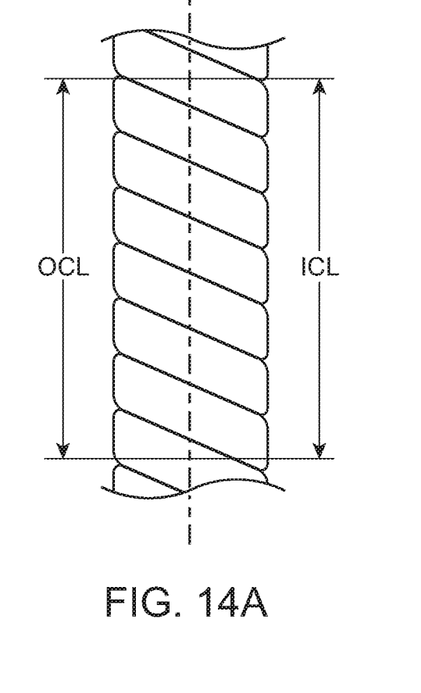
FIGS. 14A, 14B, 15A, and 15B illustrate how the designs of the inner and outer sleeves maintain dimensional stability of the push-pull cables of the present invention when entering and leaving a curved section of a deployment tool.
Figure 14B:
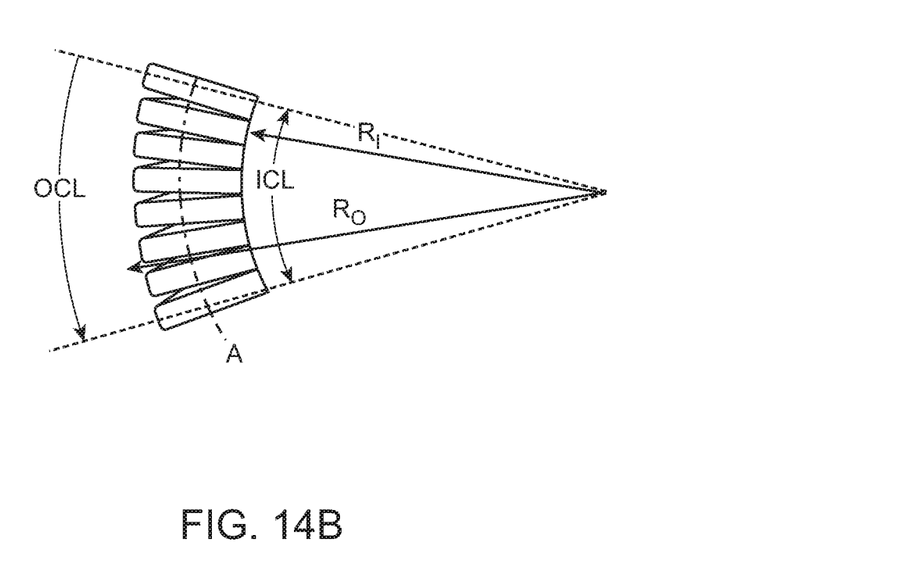
Figure 15A:
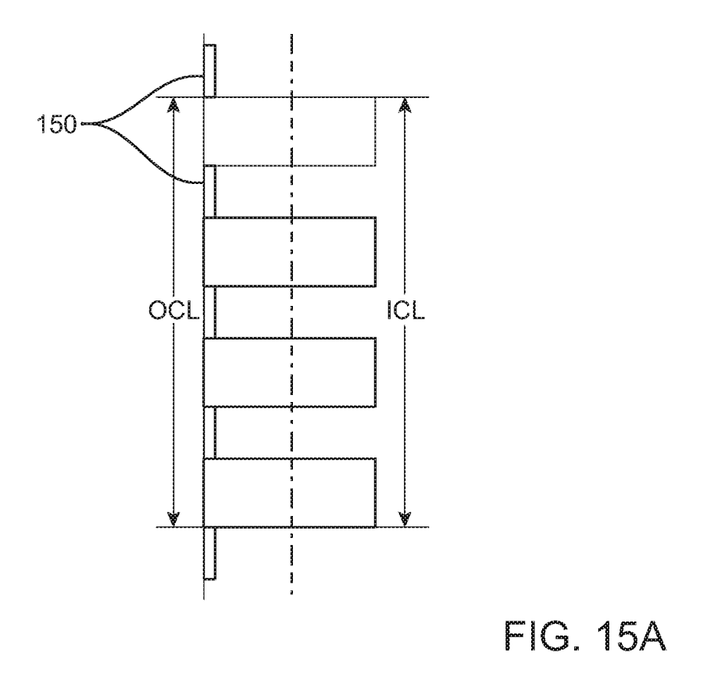
Figure 15B:
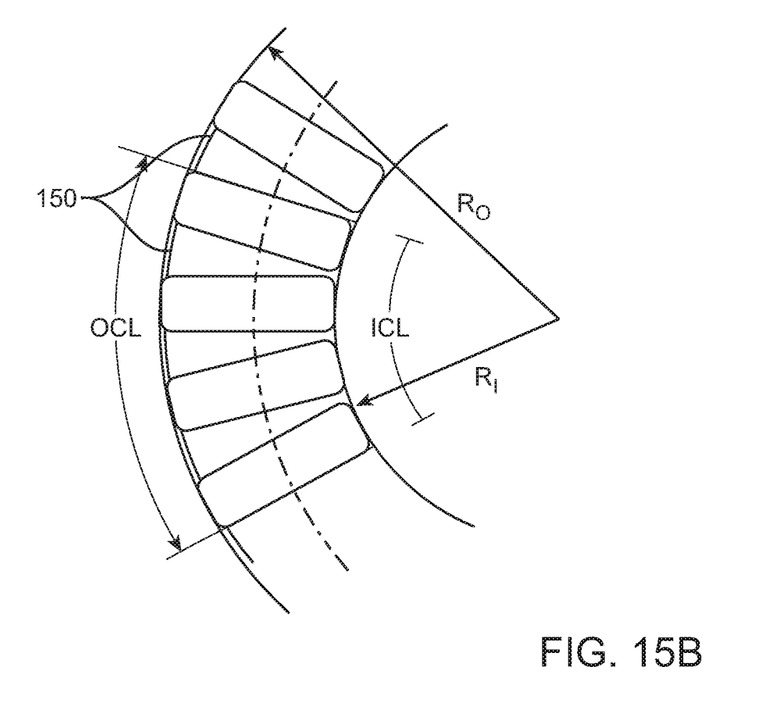

After the assembly of the outer sleeve 124 and inner sleeve 136 has been placed into the curved forming mandrel 152, the inner sleeve 136 will be pushed distally relative to the outer sleeve 124 in order to axially elongate and tension the outer sleeve as shown by the arrows in FIG. 13. Sufficient tension will be applied to axially separate adjacent segments 126 to the extent possible. In particular, in regions where the outer sleeve is generally straight, the adjacent segments 126 will be able to fully separate, e.g. to the extent shown in FIG. 7A above. In other segments, however, which are constrained within the forming mandrel 152, at least some of the adjacent segments 126 will be bent relative to each other, and the individual tabs and slots will be in particular configurations dictated by the curvature, such as shown for example in FIG. 7A through 7D.

After fully tensioning the outer sleeve 124 by internally advancing the inner sleeve 136, the proximal end of the outer sleeve will be fixed to a proximal end or portion of the inner sleeve 136. For example, a solder region 156 may be applied to the distal rigid end segment 130 of the outer sleeve and to an adjacent portion of the inner sleeve 136.

After the outer sleeve 124 is tensioned relative to the inner sleeve while configured in a desired curvature, as shown in FIG. 12, and the ends of the outer sleeve and inner sleeve fixed or connected together, the completed flexible cable sheath may be withdrawn from the curved forming mandrel. When removed from the curved forming mandrel, the outer sleeve 124 will no longer be fully tensioned as the sheath straightens. However, when introduced to a tool having the same curvature as the forming tool 152, the flexible cable sheath will again be tensioned so that it again becomes dimensionally stable and torsionally rigid. Moreover, the flexible cable sheath can be axially advanced and retracted through the curved segment of the tool while maintaining the desired dimensional stability and torsional rigidity. Segments outside of the curve will remain fully axially separated while those within the curve will be able to bend and unbend as needed while passing through the curved region.

Referring now to FIGS. 14A, 14B, 15A, and 15B, to maintain dimensional stability when the push-pull sheath is advanced and retracted over a curve, an inner curved length ICL of the coiled inner sleeve (FIGS. 14A and 14B) and an outer curved length OCL of the segmented outer sleeve (FIGS. 15A and 15B) are each configured to resist a change the axial length. The inner curved length ICL of the coiled inner sleeve cannot shorten as the successive turns of the coil have no gaps to permit such shortening. The OCL of the outer sleeve, in contrast, cannot axially elongate since the adjacent segments are linked together by the tabs and slots shown schematically as elements 150 in FIGS. 15A and 15B. Conversely, the outer OCL of the coiled inner sleeve is configured to allow axial elongation (FIGS. 14A and 14B) and the inner curved length of the outer sleeve is configured to allow axial compression (FIGS. 15A and 15B) when the push-pull sheath is advanced and retracted over a curve. It is these properties of the inner and outer sleeves that allow the push-pull sheath to maintain its axial length without appreciable shortening or lengthening after the length is set to accommodate any given curve in a shaft which carries the push-pull sheath.

Any fixed curve in a shaft carrying the sheath between straight segments (as shown at 16 in FIG. 1) involves specific number of segments in the outer sleeve and coils in the inner sleeve. At any time, when the flexible cable sheath is advanced or withdrawn within the curved tubing in the deployment shaft, the number of coils and the number of links within the curved tubing will remain the same, although the specific segments and coils will change as some exit the curve and a like-number enters the curve. When the flexible cable sheath is advanced from straight into the curved segment of the c-arm the axial length of the coil expands in the direction of the sheath movement while the outside sleeve shortens (as described above). This allows the adjacent surfaces of the outer sleeve and inner sleeve to slide over each other while the sheath is advanced or withdrawn within the curved segment of the shaft. The outside sleeve and inner coil do not move in relation to each other in straight segments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A push-pull cable assembly comprising;
  (a) a flexible cable sheath comprising:
    an outer sleeve having a proximal end, a distal end, and a central lumen extending between said ends, wherein said outer sleeve includes a plurality of individual segments and wherein axially adjacent individual segments are coupled to limit axial separation and to allow bending; and
    an inner sleeve disposed within the central lumen of the outer sleeve and having a proximal end, a distal end, and an inner lumen extending between said ends;
    wherein said outer and inner sleeves are fixed to each other at their proximal and distal ends, respectively, with the outer sleeve axially tensioned over the inner sleeve; and
    wherein the inner lumen of the inner sleeve is configured to slidably receive a push-pull cable; and (b) a push-pull cable slidably received within the inner lumen of the inner sleeve.

2. A push-pull cable assembly as in claim 1, wherein the axially adjacent individual segments are coupled to limit relative rotational movement.

3. A push-pull cable assembly as in claim 1, wherein at least a portion of the push-pull cable sheath is configured to pass through a preselected arc, wherein the axially adjacent individual segments are tensioned when the push-pull cable sheath is deformed in the arc and are not tensioned when the push-pull cable sheath is straight.

4. A push-pull cable assembly as in claim 1, wherein axially adjacent individual segments are joined by tabs and slots, wherein a tab on one individual segment is received in a slot on an adjacent individual segment.

5. A push-pull cable assembly as in claim 4, wherein the tab comprises a T-tab and the slot comprises a T-slot.

6. A push-pull cable assembly as in claim 4, wherein the tab comprises a disc and the slot comprises a circular void.

7. A push-pull cable assembly as in claim 4, wherein the tab and slot have axial clearance to permit axial movement between axially adjacent segments and the tab and slot have lateral clearance to permit bending between axially adjacent segments.

8. A push-pull cable assembly as in claim 1, wherein the axially adjacent individual segments are arranged in a cylindrical pattern when the outer sleeve is in a straightened configuration.

9. A push-pull cable assembly as in claim 8, wherein the outer sleeve comprises a cut or patterned tube.

10. A push-pull cable assembly in claim 9, wherein the outer sleeve comprises a laser cut metal tube.

11. A push-pull cable assembly as in claim 1, wherein the inner sleeve comprises a helical coil.

12. A push-pull cable assembly as in claim 11, wherein the helical coil comprises round wire.

13. A push-pull cable assembly as in claim 11, wherein the helical coil comprises a flat ribbon.

14. A push-pull cable assembly as in claim 11, wherein the inner sleeve comprises counter wound helical coils.

15. A laparoscopic tool comprising;
   a shaft having a distal end, a proximal end, and a central passage therethrough;
   a flexible push-pull cable sheath as in claim 1 passing through the central passage with a distal end of the push-pull cable sheath extending beyond the distal end of the shaft and a proximal end of the push-pull cable sheath extending beyond the proximal end of the shaft;
   a push-pull cable slidably received within the inner lumen of the inner sleeve;
   a handle secured to the proximal end of the push-pull cable sheath and operatively coupled to a proximal end of the push-pull cable;
   a tool secured to a distal end of the push-pull cable sheath and operatively coupled to a distal end of the push-pull cable so that tension applied to the push-pull cable actuates the tool.

16. A laparoscopic tool as in claim 15, wherein the shaft has an arcuate section, and wherein tension on the flexible push-pull cable sheath is adjusted so that adjacent segments of the flexible push-pull cable sheath can bend relative to each other while being advanced or retracted through the arcuate section while the entire length of the flexible push-pull cable sheath remains under tension and resists both stretching and axial compression.

17. A laparoscopic tool as in claim 15, further comprising a lever on the handle attached to the proximal end of the push-pull cable, said lever configured to selectively apply axial tension to the push-pull cable to actuate the tool.

18. A laparoscopic tool as in claim 16, wherein the shaft has telescoping sections on each side of the arcuate section, wherein the telescoping section on one end of the arcuate section will extend axially when the end flexible push-pull cable is advanced to collapse the telescoping section on the other side of the arcuate section.

\* \* \* \* \*